(12) United States Patent
Fahnenstich

(10) Patent No.: US 8,979,439 B2
(45) Date of Patent: Mar. 17, 2015

(54) ELECTRODE MILLING CUTTER WITH MILLING EDGES INTERRUPTED BY CUT-OUTS

(75) Inventor: Stefan Fahnenstich, Gröbenzell (DE)

(73) Assignee: Lutz Precision, k.s., Bratislava (SK)

( * ) Notice: Subject to any disclaimer, the term of this patent is extended or adjusted under 35 U.S.C. 154(b) by 1223 days.

(21) Appl. No.: 12/747,695

(22) PCT Filed: Dec. 10, 2008

(86) PCT No.: PCT/EP2008/010479
§ 371 (c)(1),
(2), (4) Date: Feb. 28, 2011

(87) PCT Pub. No.: WO2009/074306
PCT Pub. Date: Jun. 18, 2009

(65) Prior Publication Data
US 2011/0150581 A1    Jun. 23, 2011

(30) Foreign Application Priority Data

Dec. 12, 2007    (DE) .................... 20 2007 017 307 U
May 29, 2008    (DE) .................... 20 2008 007 251 U

(51) Int. Cl.
*B26D 1/12*    (2006.01)

(52) U.S. Cl.
USPC .................. 407/30; 407/56; 407/62

(58) Field of Classification Search
USPC .................. 407/56, 62, 61, 30, 34, 115, 116; 83/472, 483, 486, 592
See application file for complete search history.

(56) References Cited

U.S. PATENT DOCUMENTS

| | | | | |
|---|---|---|---|---|
| 1,472,960 | A * | 11/1923 | Conklin | 407/29 |
| 4,161,972 | A * | 7/1979 | Hanaya | 144/176 |
| 4,551,918 | A * | 11/1985 | Smithberg | 30/347 |
| 4,750,849 | A * | 6/1988 | Phillips | 409/131 |
| 4,934,879 | A * | 6/1990 | van Barneveld | 407/66 |
| 5,890,854 | A * | 4/1999 | Naumann et al. | 409/132 |
| 6,221,076 | B1 * | 4/2001 | Albrektsson et al. | 606/80 |
| 7,373,707 | B2 * | 5/2008 | Ouchiyama et al. | 29/33.5 |
| 7,510,589 | B2 * | 3/2009 | Bruck et al. | 55/525 |
| 2004/0265075 | A1 * | 12/2004 | Kolker | 407/113 |
| 2008/0078749 | A1 | 4/2008 | Sigler et al. | |
| 2012/0093593 | A1 | 4/2012 | Lutz | |

FOREIGN PATENT DOCUMENTS

| | | |
|---|---|---|
| DE | 197 50 312 A1 | 5/1999 |
| DE | 202 08 350 U1 | 10/2002 |
| DE | 203 15 288 U1 | 3/2005 |

(Continued)

OTHER PUBLICATIONS

Jun. 24, 2010 International Preliminary Report in priority PCT/EP2008/010479.

(Continued)

*Primary Examiner* — Omar Flores Sanchez
(74) *Attorney, Agent, or Firm* — Novak Druce Connolly Bove + Quigg

(57) ABSTRACT

Electrode milling cutter for machining spot welding electrodes, said electrode milling cutter having one or more milling edges, wherein at least one of the milling edges is interrupted by one or more cut-outs at one or more points. The invention also relates to a milling device and to an apparatus for subsequently machining spot welding electrodes.

20 Claims, 10 Drawing Sheets

(56) References Cited

FOREIGN PATENT DOCUMENTS

| DE | 202008007251 U1 | 6/2012 |
|---|---|---|
| FR | 2 846 897 A | 5/2004 |
| WO | WO2009095237 A1 | 8/2009 |

OTHER PUBLICATIONS

Jul. 15, 2010 Translation of the International Preliminary Report on patentability in priority PCT/EP2008/010479.

In the case of a German Utility Model related to U.S. Appl. No. 12/747,695, applicant received a Cancellation Request (attached). Cancellation is requested with the following short reasoning of the representative (English translation in quotes).

2. The subject-matter of this Utility Model is not protectable as a Utility Model; the invention is not novel, but corresponds to the state of the art and is described in many papers and is frequently used in practice. I refer to the "Handbuch der Fertigungstechnik Band 3/1 Spanen, G. Spur and Th. Stoferle 1979". There it is disclosed "Cutting inserts with cut-outs for machining do not require a chip former. A cut-out for machining (different products have different forms of cut-outs)." A variation of the distances, width or depth of the cut-outs does not include an inventive step.

"3. The invention in dispute is also the subject-matter of the patent application with the international reference sign PCT/EP2009/000575. In the international search report for it dated Apr. 27, 2009 it is determined that the claims are partly comprised in publications defining the state of the art which are not considered to be of particular relevance, and partly in publications of particular relevance, based on which the invention cannot be considered as novel or based on an inventive step."

The application PCT/EP2009/000575 (published as WO 2009/095237) was filed in Jan. 2009 and appears to relate to a different invention.

German Search Report for Applicaton No. 20 2007 017 307.5, dated Oct. 13, 2008.

First Office Action mailed Dec. 4, 2012 in corresponding CN Application No. 200880125094.8.

Apr. 29, 2009 International Search Report in priority PCT/EP2008/010479.

Sep. 4, 2013 Office Action in corresponding CN 200880125094.8 with English translation (citing FR 2846897 B1) already of record).

* cited by examiner

ELECTRODE MILLING CUTTER WITH MILLING EDGES INTERRUPTED BY CUT-OUTS

FIELD OF THE INVENTION

The invention relates to an electrode milling cutter for machining spot welding electrodes and a milling device for subsequently machining worn down spot welding electrodes and an apparatus for subsequently machining spot welding electrodes.

BACKGROUND

To firmly connect sheet metal parts, in industrial plants, such as for example automobile manufacturing plants, welding robots with welding guns are often employed. During a welding operation, the welding gun presses two or several sheet metal parts against each other from two opposite sides while electric current flows through spot welding electrodes mounted in the gun arms of the welding gun, so that the sheet metal parts are welded to each other with utmost precision. The closing force of a spot welding gun during the welding operation can add up to 8 kN. After approx. 100 to 300 welding operations, the spot welding electrodes are worn down or coated with welding residues to such an extent that reliable welding is no longer possible.

Usually, the welding electrodes comprise exchangeable caps. However, they can also be made in one piece without such caps. The following explanations likewise concern both cases as the milling cutter, the milling device and the apparatus can be equally employed for one-piece electrodes and for electrodes with caps.

To return the worn down spot welding electrode tips again to their original shape, said tips are subsequently machined by means of an electrode milling cutter. To repair the worn down spot welding electrodes that consist of relatively soft copper, it is in most cases sufficient to remove less than 0.1 mm of material from the spot welding electrode tips.

With electrode milling cutters as they are known from prior art, however, double or triple amount of this thickness (0.2 mm to 0.3 mm) is removed in practice. On the one hand, this leads to the copper electrodes being shortened to an unnecessarily great extent, so that the electrodes or the electrode caps must be completely replaced correspondingly earlier. On the other hand, the unnecessarily substantial removal also leads to a corresponding increase of the amount and size of the removed copper chips, thus increasing the risk of the milling cutter getting clogged. The replacement of spot welding electrodes or the cleaning of an electrode milling cutter usually results in the complete welding operation having to be interrupted for quite a long time, leading to considerable follow-up costs due to loss of production or rejects being produced.

To reduce the material removal during the milling of the spot welding electrodes, it would be conceivable to have the welding guns, which grip with the spot welding electrodes into the electrode milling device for milling off, grip into the electrode milling device either shorter or with a lower force of pressure. In practice however, it is difficult to realize such a procedure as the closing time of spot welding guns can be hardly reduced to below 0.7 s and thus milling time cannot be shortened arbitrarily. It is equally difficult to clearly reduce the closing force of 1 to 2 kN as this would result in positioning inaccuracies, such as e.g. the welding arms bending less at a reduced force of pressure, whereby the orientation of the active areas with respect to each other changes.

It would be furthermore conceivable to reduce the amount removed during milling by selecting the speed of the electrode milling cutter to be lower than the usual 200 to 700 rpm, or by selecting the tool clearance at the milling edge or edges of the milling cutter to be smaller than the 6° usual for non-ferrous heavy metal. Both of these possible modifications, however, would lead to clearly worse milling results, such as irregular material removals, vibrations during the milling operation or a poor machining result.

SUMMARY OF THE INVENTION

The object underlying the invention described below is to extend the service life of spot welding electrodes by only removing as much material as is required (for example less than 0.1 mm) during the subsequent machining of worn down spot welding electrodes.

This object is achieved with an electrode milling cutter, a milling device and an apparatus.

The explanations as to electrode caps correspondingly also apply to electrodes without caps and vice versa.

The electrode milling cutter for machining spot welding electrodes comprises at least one milling edge, such as the edge of a metal part, which is characterized according to the invention in that said milling edge is interrupted at one or several points by one or several cut-outs. The use of such an electrode milling cutter results in annular swellings being formed at the spot welding electrodes at points of the cut-outs during milling. This for example leads to a thinner layer of the spot welding electrode material being removed during milling, whereby the service life of a spot welding electrode can be extended several times over. Moreover, the use of milling edges with interruptions lead to smaller chips or milling particles being generated during milling, which clearly reduces the risk of the milling cutter getting clogged. Furthermore, the annular swellings formed during milling with the electrode milling cutter according to the invention permit a more precise positioning of the spot welding electrode tip in the electrode milling cutter as the swellings on the electrode and the cut-outs somewhat engage each other. Finally, one can see by the positions of said swellings when a spot welding electrode is completely worn down and therefore has to be replaced.

In a preferred embodiment of the invention, the width as well as the depth of the cut-outs is 30 μm to 110 μm or maximally 0.5, 1.0 or 1.5 mm. Depending on the number of cut-outs per milling edge, however, larger or smaller dimensions are also conceivable. Moreover, the cut-outs of one or various milling edges do not necessarily all have to be identical but can rather have different sizes.

The distance of adjacent cut-outs, usually within a range of 1 to 5 mm, however, can be larger or smaller, depending on the application. The distances between respective adjacent cut-outs can each be identical or vary.

In one preferred embodiment of the invention, a milling edge is interrupted by three cut-outs. In electrode milling cutters for very small spot welding electrodes, however, it is also possible to only have one or two cut-outs, and in electrode milling cutters for large spot welding electrodes, the number of cut-outs per milling edge can be four or more.

The concrete selection of the number, dimensions and distances of the cut-outs mainly depends on the spot welding task and the resulting wear of the electrodes.

A further aspect of the electrode milling cutter is that there are no cut-outs in the portion of the milling edge facing the axis of rotation, and said portion usually amounts to at least 30% of the whole length of the milling edge. Thereby, the spot welding electrodes can be as smooth as possible in the region of the active areas (contact areas), so that no change of the welding result is caused by the swellings on the welding electrodes. If the electrode milling cutter comprises several milling edges it is also possible—aside from the possibility of using identical milling edges—to use different milling edges with differently designed cut-outs or to use some milling edges without any cut-outs.

It is furthermore possible that the cut-outs along a milling edge which is part of a milling element are designed such that the milling element is completely interrupted by the cut-outs. Moreover, several milling elements are conceivable which are arranged next to each other such that a milling edge with one or several interruptions is formed.

The electrode milling cutter can furthermore comprise a mounting socket for guiding a spot welding electrode to be machined. In this embodiment of the invention, the milling edges are fixed at or in the mounting socket.

The cut-outs might be partially located underneath the surface of a corresponding mounting socket, that means that a portion of the volume of a cut-out is located above the surface of the mounting socket, and a portion of the volume of said cut-out is located underneath the surface of the mounting socket. It is furthermore possible for the lower part of a cut-out to be located at the same level as the surface of the mounting socket, so that an approximately smooth or even surface is present in the region of said cut-out. Such an arrangement of the elements of an electrode milling cutter makes it possible that during the milling operation, the spot welding electrode to be machined rests directly on the mounting socket in the region of such a cut-out. It is thereby possible to further reduce the material removal of a spot welding electrode in the milling operation.

Typically, approximately two thirds of the volume of a cut-out are located underneath the surface of a mounting socket. The volume above the surface of the mounting socket is preferably at least one fifth, one fourth, one third or half of the volume of the cut-out. The volume underneath the surface of the mounting socket should be at least one fifth, one fourth, one third or half of the volume of the cut-out. Normally, all cut-outs have this property. However, combinations are also conceivable where some of the cut-outs are located completely above the surface, partially above the surface and at the same level with the surface of the mounting socket. Furthermore, the cut-outs can comprise rounded or blunt edges, whereby equally an additional reduction of the material removal of a spot welding electrode during the milling operation is possible.

Furthermore, the electrode milling cutter according to the invention is usually a component of a milling device for subsequently machining worn down spot welding electrodes. Such a milling device normally comprises, in addition to the electrode milling cutter, a drive motor and possibly a transmission for a speed of 200 to 700 rpm of the milling cutter. The output of this drive motor is typically within a range of 0.3 to 2 kW.

The invention furthermore relates to an apparatus for machining electrodes using one of the electrode milling cutters described above or below, and the milling device.

It is moreover possible to carry out a method for subsequently machining spot welding electrodes wherein an electrode milling cutter or a milling device according to one of the preceding descriptions is used.

Further aspects of preferred and possible embodiments of the invention will become clear with reference to the drawing.

DETAILED DESCRIPTION

Figure 1A:
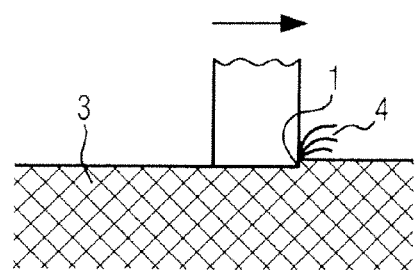
FIG. 1a shows a schematic view of a milling operation.
Figure 1B:
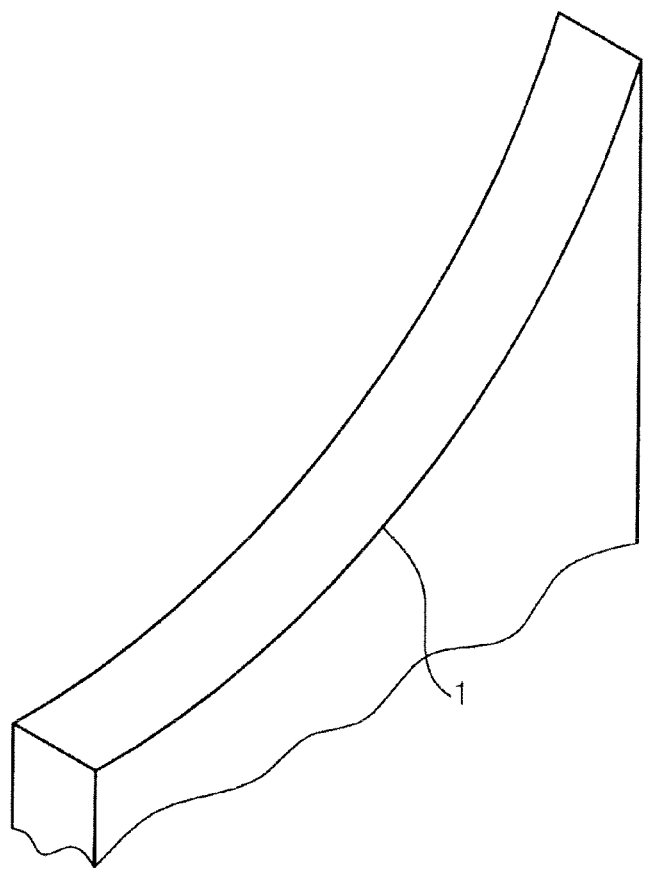
FIG. 1b shows a schematic view of a milling element with a milling edge (not according to the invention)

FIG. 1a schematically shows a milling operation by means of a milling edge 1 which is moved over the surface of the material 3 in a direction of the arrow, so that material is removed, typically in the form of chips 4. A milling element with a continuous milling edge 1 as it is used in prior art is drawn in FIG. 1b.

FIGS. 2 to 5 show milling elements with milling edges 1 according to the invention which are interrupted by cut-outs 2.

The cut-outs are shown here and in the other figures with a rectangular cross-section. However, rounded or half-round or differently shaped cross-sections are also possible. For example, a cut-out can have a cross-section which is composed of three circular arc sections, so that, for example, the cross-section of such a cut-out is shaped to be concave in the middle and convex in the marginal areas.

Figure 2:
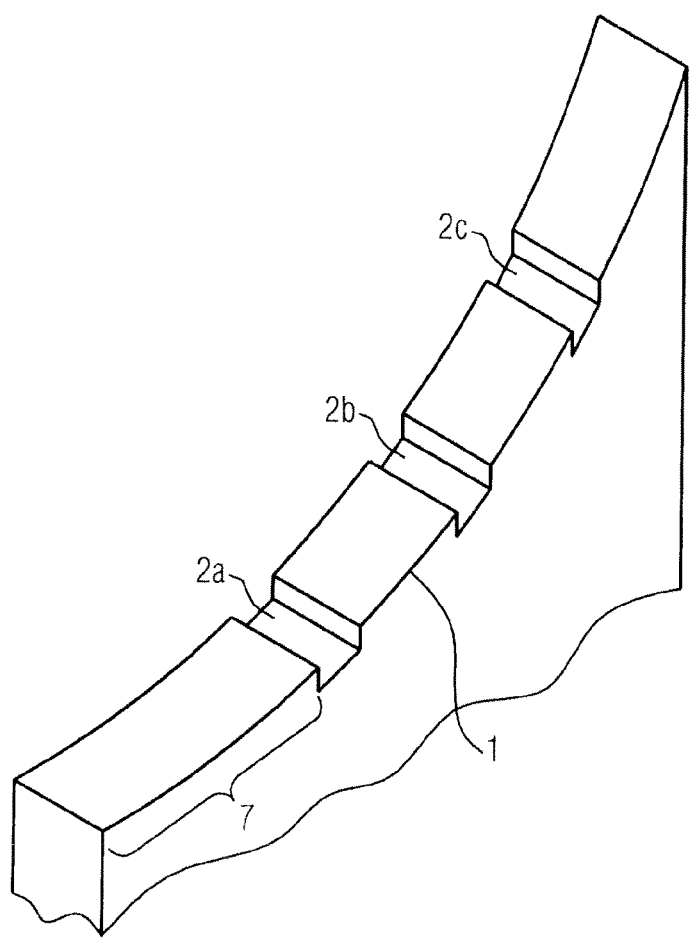
FIG. 2 shows a schematic view of a milling element with a milling edge which is interrupted by cut-outs.

In the case of FIG. 2, the milling edge 1 is interrupted by the cut-outs 2a, 2b and 2c which all have the same dimensions and have constant distances to the respective adjacent cut-outs. Furthermore, in FIG. 2 a region 7 of the milling edge 1 which is free from cut-outs 2 is indicated. Typically, the region 7 that is free from cut-outs is that portion of the milling edge 1 which faces the center of the electrode milling cutter or which is closest to the axis of rotation of the electrode milling cutter. The non-existence of cut-outs in the region 7 ensures that spot welding electrodes are milled to be as smooth as possible in the region of the tip.

Figure 3:
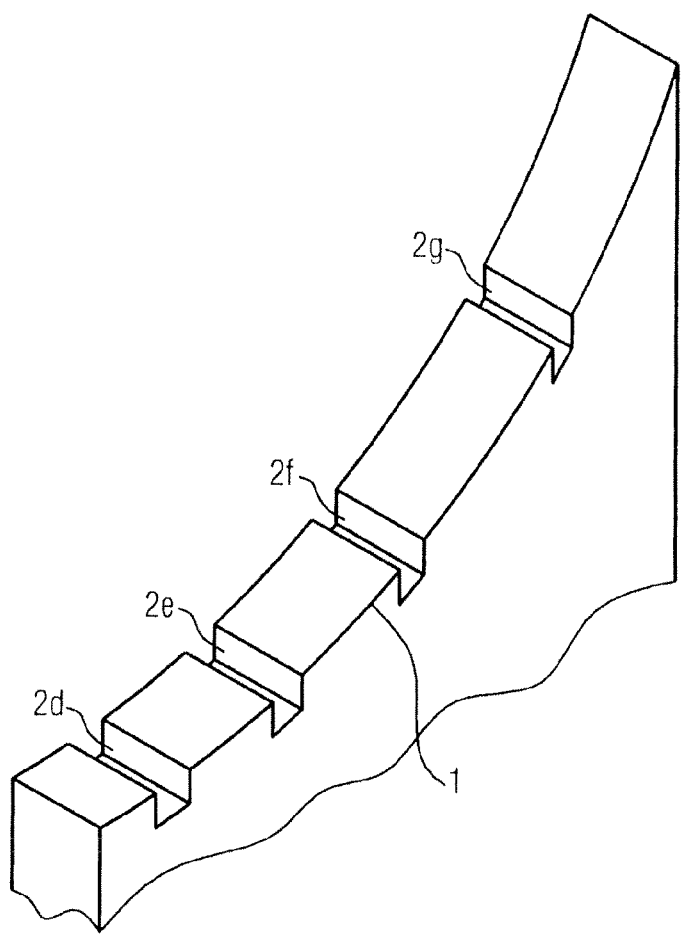
FIG. 3 shows a schematic view of a milling element with a milling edge which is interrupted by cut-outs.

In FIG. 3, a milling edge 1 with four cut-outs (2d to 2g) is shown, the distances between respective adjacent cut-outs each being different. By the selection of the distances, the local density of the cut-outs 2 along a milling edge 1 is determined. The density of the cut-outs 2 in turn influences the milling behavior and the size of the chips formed during the milling operation.

Figure 4:
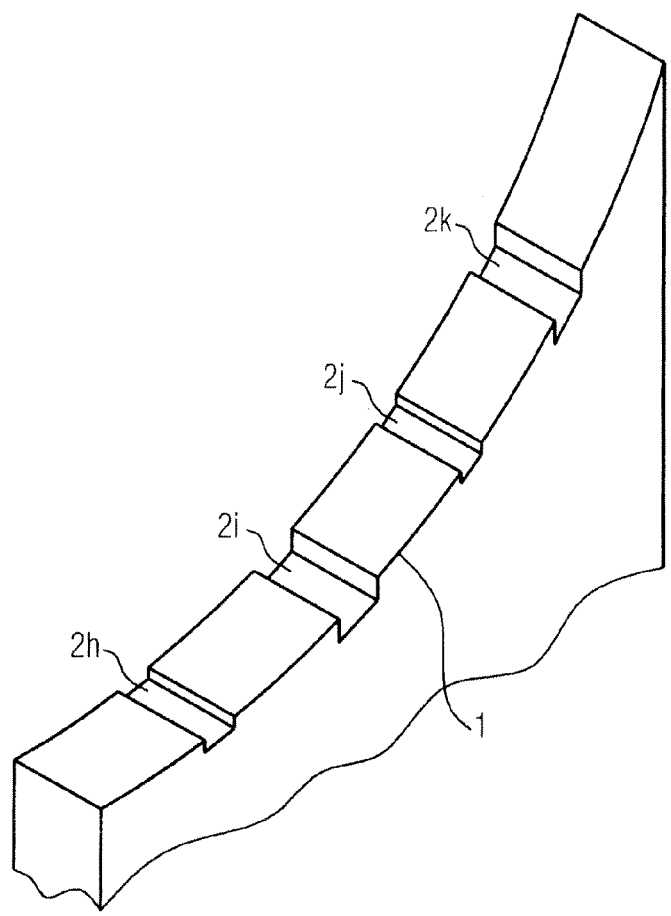
FIG. 4 shows a schematic view of a milling element with a milling edge which is interrupted by cut-outs.

Furthermore, FIG. 4 shows a case where the milling edge 1 is interrupted by the cut-outs 2h to 2k, some of the dimensions of the cut-outs being different and some being identical. The dimensions of the cut-outs 2h and 2j are identical, and the cut-outs 2i and 2k are identical, however, the cut-outs 2i and 2k are larger than the cut-outs 2h and 2j. Larger cut-outs make sense, for example, if a particularly distinct swelling is to be formed at a spot welding electrode to be machined for a more accurate positioning of the spot welding electrode in a cap milling cutter.

Figure 5:
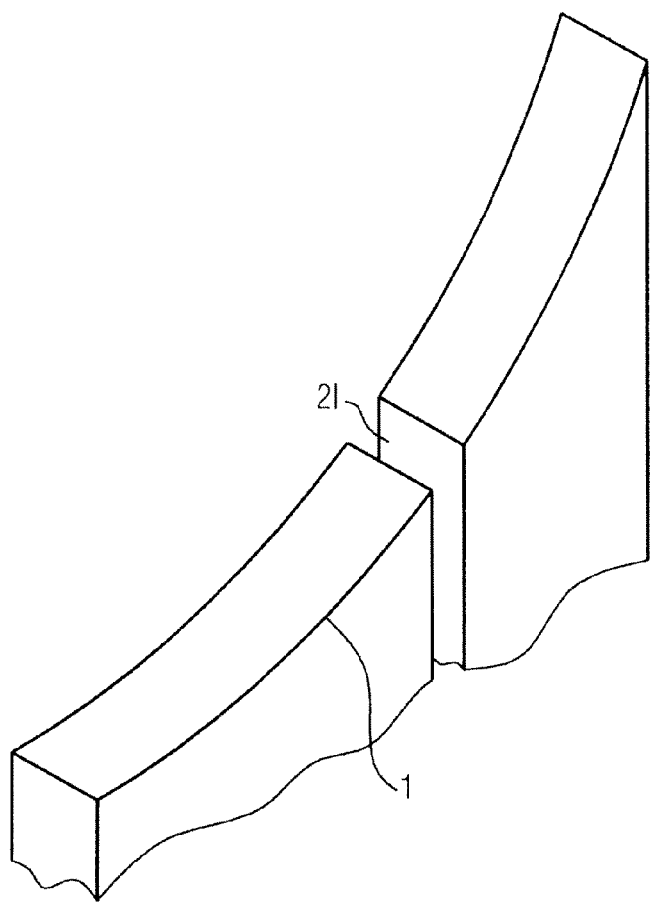
FIG. 5 shows a schematic view of a milling element with a milling edge which is interrupted by cut-outs.

FIG. 5 shows a milling element with a milling edge 1 that is interrupted by the cut-out 2*l* such that the milling element is divided into two parts. It is also possible to interpret FIG. 5 to the effect that two milling elements are arranged such that one milling edge 1 is formed which is interrupted by a suitably selected distance of the two milling elements. Further interruptions of the milling edge 1 are also possible in case of completely interrupted milling elements.

Figure 6:
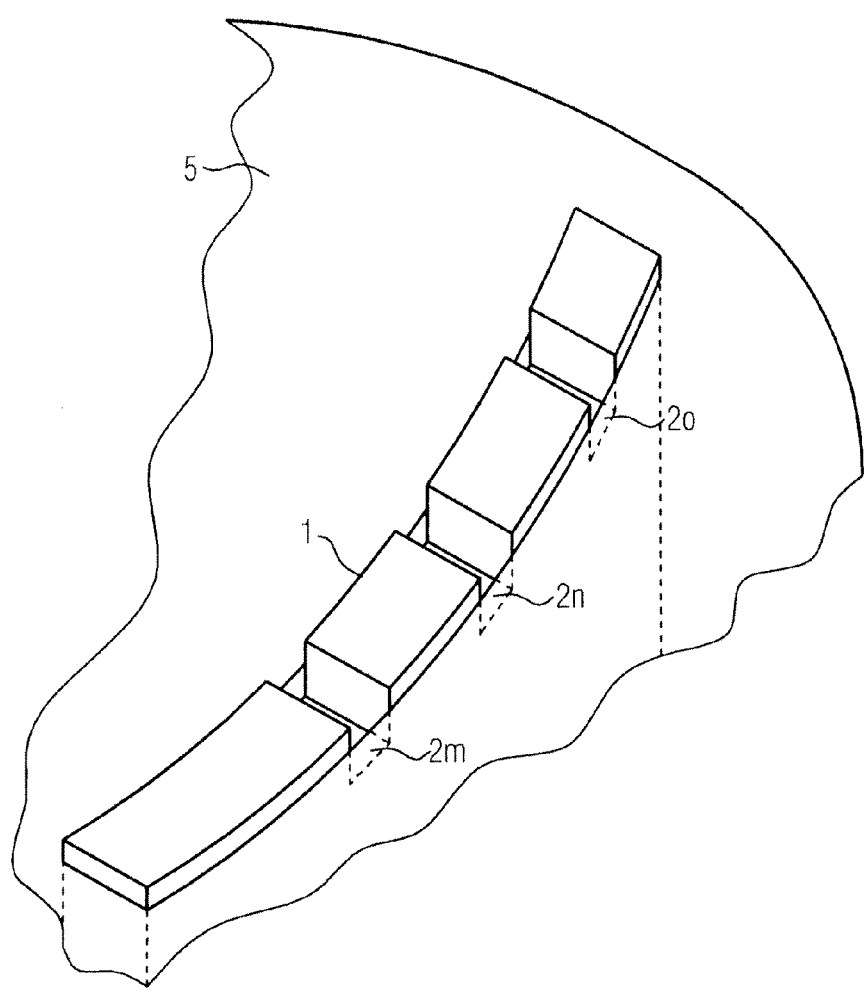
FIG. 6 shows a schematic partial view of an electrode milling cutter.

FIG. 6 shows a partial view of a cap milling tool where a milling element with a milling edge 1 and cut-outs 2*m*, 2*n* and 2*o* is mounted on or in a mounting socket such that the milling edge 1 projects from the surface of the mounting socket 5. The non-visible portion of the milling element is indicated by dotted lines. As becomes clear from FIG. 6, a portion of the cut-outs 2 is located underneath the surface of the mounting socket 5 (accordingly, the remaining portion of the cut-outs 2 remains above the surface of the mounting socket 5). However, embodiments where the cut-outs 2 are located completely above the surface of the mounting socket 5 are also possible. Furthermore, a special case where the lower surfaces of the cut-outs form an approximately closed, even or smooth surface together with the surface of the mounting socket 5 is possible.

Figure 7A:
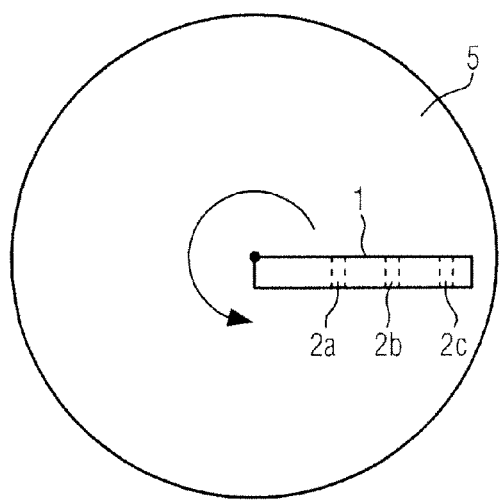
FIG. 7a shows a schematic plan view of an electrode milling cutter.
Figure 7B:
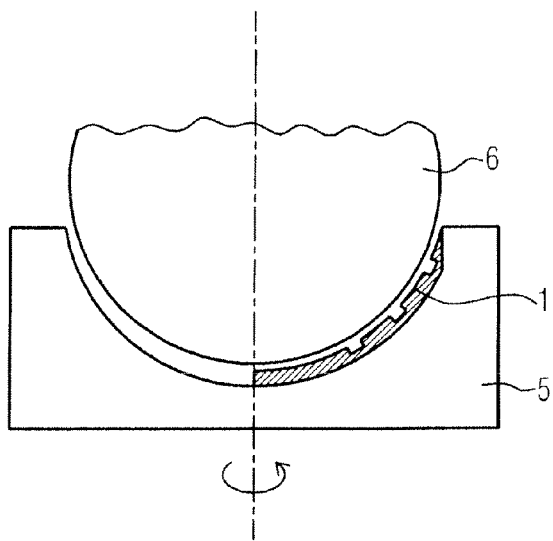
FIG. 7b shows a schematic side view of an electrode milling cutter with a spot welding electrode tip to be machined.

FIG. 7*a* shows a plan view of a cap milling tool where a milling element with a milling edge 1 and cut-outs 2*a*, 2*b* and 2*c* are mounted on or in a mounting socket, such that the milling edge 1 rotates counter-clockwise about the center of the mounting socket 5 during milling. In FIG. 7*b*, the side view of the cap milling tool of FIG. 7*a* is outlined, moreover, the tip of a spot welding electrode 6 and the axis of rotation (dotted line) are indicated in FIG. 7*b*. During the milling operation, the cap milling tool rotates about the tip of the spot welding electrode 6 (which itself does not rotate), so that the milling edge 1 removes material from the tip of the spot welding electrode 6. The mounting socket 5 mainly serves as guide for the spot welding electrode 6 on the side facing away from the milling edge 1. Typically, the axis of rotation of the cap milling tool coincides with the axis of symmetry of the spot welding electrode 6 to be machined.

The milling cutter can also be designed such that the milling element comprises two milling edges, so that both electrodes of one welding gun are machined simultaneously and with the same milling element. In FIG. 7*b*, the second milling edge would be arranged to be directed downwards. The mounting socket 5 can then also be correspondingly designed for receiving two electrodes (in FIG. 7*b* from above and from the bottom) (for example, another, approximately half-round depression can be provided from the bottom).

When the electrodes are being subsequently machined with the electrode milling cutter, the electrode can be pressed against it with a force of 1 kN to 2.5 kN. Machining time can be between 0.5 and 3.0 seconds. In subsequent machining, a milling operation can be repeated more than 50, 60 or 70 times before the electrode or the electrode cap is replaced.

Figure 7C:
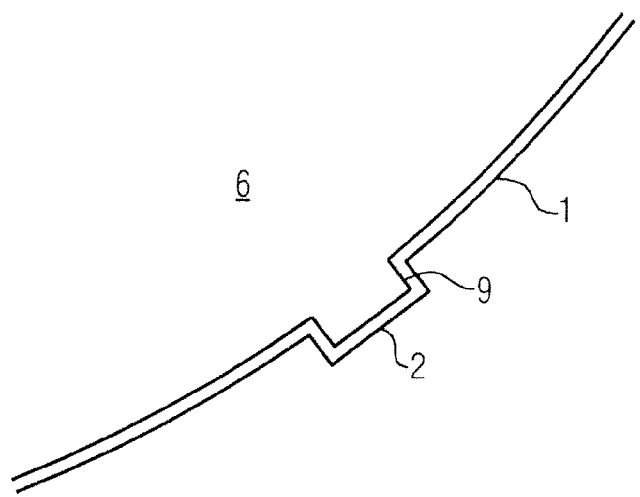
FIG. 7c shows a schematic view of a swelling and a cut-out in an enlargement.

In FIG. 7*c*, an enlargement shows how a swelling 9 is formed in a cut-out 2 of the milling edge 1. The swelling 9 guides the welding electrode 6, such that a very uniform milling result is achieved, where even in case of slight shaking between the electrode and the milling cutter, no irregular material removal occurs.

Furthermore, the swelling leads to a slowed down material removal as the milling edges do not rest on the electrode with the whole force as a portion of the force is cushioned by the swelling and the cut-out, but milling is less strong there.

Figure 7D:
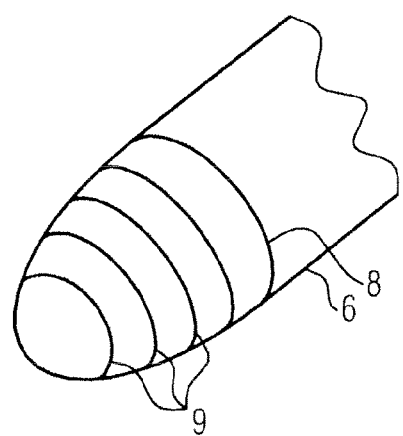
FIG. 7d shows a schematic view of a subsequently machined welding electrode.

FIG. 7*d* shows an electrode 6 with annularly arranged swellings 9. Depending on the distance between the swellings and e.g. a mark 8, one can see with the naked eye to what extent the electrode or the electrode cap is already worn down.

Figure 7E:
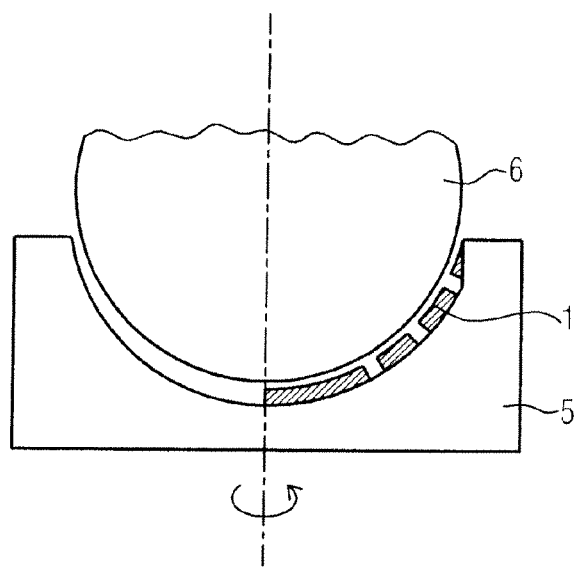
FIG. 7e shows a further schematic side view of an electrode milling cutter with a spot welding electrode tip to be machined.
Figure 8:
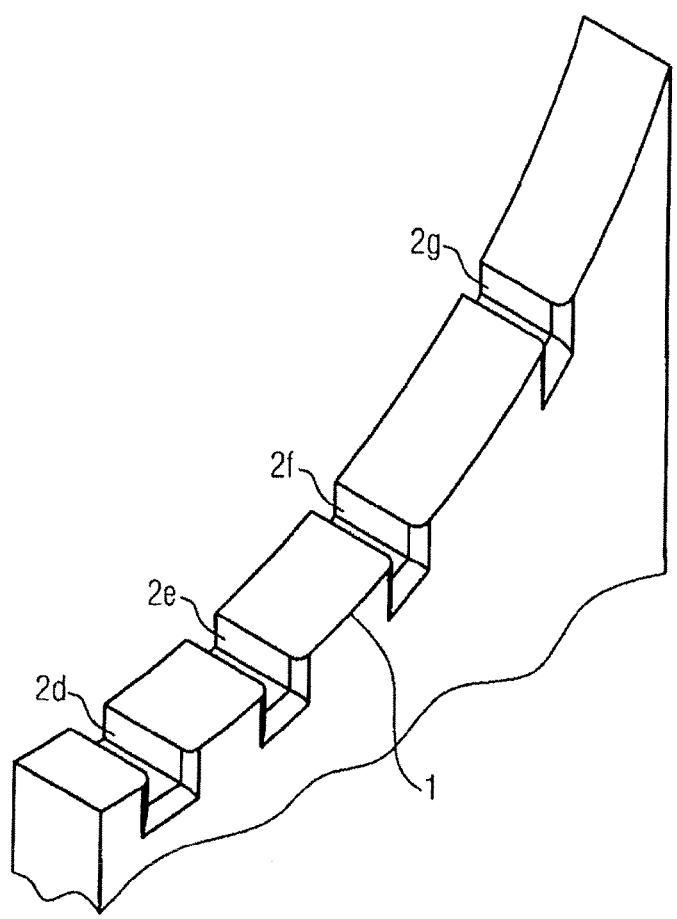
FIG. 8 shows a schematic view of a milling element with a milling edge which is interrupted by cut-outs having rounded edges.

FIG. 7*e* is analogous to FIG. 7*b*, however, the visible portion of the cut-outs 2 reaches to the surface of the mounting socket 5. It is possible for the cut-outs 2 to be either flush with the surface of the mounting socket 5, or for a portion of the volume of the cut-outs 2 to be located underneath the surface of the mounting socket 5. In both cases, the arrangement of the individual elements according to FIG. 7*e*, however, leads to the tips of spot welding electrodes 6 to be machined resting on the mounting socket 5 in the region of or near the cut-outs 2. This permits a further reduction of the electrode material removal in a milling operation.

The invention claimed is:

1. Electrode milling cutter for machining spot welding electrodes, the electrode milling cutter comprising:
   one or several milling edges;
   wherein at least one of the milling edges is interrupted at one or several points by one or several cut-outs;
   a mounting socket for guiding a spot welding electrode to be machined, wherein the milling edges are attached at or in the mounting socket;
   wherein at least one cut-out is located partially underneath the surface of the mounting socket, so that spot welding electrodes to be machined rest on the mounting socket in the region of the at least one cut-out.

2. Electrode milling cutter according to claim 1, wherein the width of the cut-outs is within a range above a minimum value selected from the group consisting of 30 μm, 40 μm, 50 μm, 60 μm, 70 μm, 80 μm, 90 μm, 100 μm, 200 μm, 400 μm, 800 μm, or 1200 μm and/or below a maximum value selected from the group consisting of 40 μm, 50 μm, 60 μm, 70 μm, 80 μm, 90 μm, 100 μm, 110 μm, 220 μm, 440 μm, 880 μm or 1400 μm.

3. Electrode milling cutter according to claim 1, wherein the depth of the cut-outs is within a range above a minimum value selected from the group consisting of 30 μm, 40 μm, 50 μm, 60 μm, 70 μm, 80 μm, 90 μm, 100 μm, 150 μm, 200 μm, 250 μm or 300 μm, and/or below a maximum value selected from the group consisting of 40 μm, 50 μm, 60 μm, 70 μm, 80 μm, 90 μm, 100 μm, 110 μm, 200 μm, 250 μm, 300 μm or 400 μm.

4. Electrode milling cutter according to claim 1, wherein the distance between adjacent cut-outs is within a range above a minimum value selected from the group consisting of 0.5 mm, 1 mm, 2 mm, 3 mm, 4 mm, 5 mm, 6 mm, 7 mm, 8 mm or 9 mm, and/or below a maximum value selected from the group consisting of 1 mm, 2 mm, 3 mm, 4 mm, 5 mm, 6 mm, 7 mm, 8 mm, 9 mm or 10 mm.

5. Electrode milling cutter according to claim 1, wherein all cut-outs of a milling edge have the same dimensions, or at least one cut-out has other dimensions than another cut-out.

6. Electrode milling cutter according to claim 1, wherein the distances between adjacent cut-outs are each identical, or the distances are at least partially different.

7. Electrode milling cutter according to claims 1, wherein the number of cut-outs per milling edge is more, less or equal to 1, 2, 3, 4, 5, 6, 7 or 8.

8. Electrode milling cutter according to claim 1, wherein no cut-outs are located in a portion of the milling edge facing an axis of rotation.

9. Electrode milling cutter according to claims 1, wherein all milling edges comprise the same cut-outs with the same distances.

10. Electrode milling cutter according to claim 1, wherein different milling edges comprise cut-outs at at least partially different points.

11. Electrode milling cutter according to claims 1, wherein only some milling edges are provided with cut-outs.

12. Electrode milling cutter according to claims 1, wherein the cut-out are designed such that a milling element comprising the milling edge is completely interrupted.

13. Electrode milling cutter according to claim 1, wherein a volume of the at least one cut-out, located beneath the surface of the mounting socket, is selected has a minimum value selected from the group consisting of at least 10%, 20%, 30%, 40%, 50%, 60%, 70% or 80.

14. Electrode milling cutter according to claim 1, wherein all cut-outs of a milling edge are located partially underneath the surface of the mounting socket.

15. Electrode milling cutter according to claim 1, wherein at least one cut-out is designed such that the lower region of the at least one cut-out forms a nearly continuous plane with the surface of the mounting socket.

16. Electrode milling cutter according to claims 1, wherein the cut-outs comprise a rectangular, rounded or half-round cross-section.

17. Electrode milling cutter according to claim 1, wherein one or several cut-outs comprise rounded edges.

18. Milling device for subsequently machining spot welding electrodes, the milling device comprising:
 an electrode milling cutter according to claim 1; and
 a drive motor with one transmission for 200 to 700 revolutions per minute of the electrode milling cutter and/or a motor output of 0.3 to 2 kW.

19. Apparatus for subsequently machining spot welding electrodes, including the milling cutter according to claim 1, and wherein the electrode milling cutter comprises milling edges interrupted by cut-outs.

20. Electrode milling cutter according to claim 13, wherein a volume of the at least one cut-out, located beneath the surface of the mounting socket has a maximum value selected from the group consisting of 20%, 30%, 40%, 50%, 60%, 70%, 80% or 90%.

* * * * *